United States Patent [19]

Häkkinen

[11] 4,299,355
[45] Nov. 10, 1981

[54] APPARATUS FOR ATOMIZING MEDICAMENTS

[76] Inventor: Taisto Häkkinen, Kaarlonkatu 25, 13210 Hämeenlinna 21, Finland

[21] Appl. No.: 111,071

[22] Filed: Jan. 3, 1980

[30] Foreign Application Priority Data

Jan. 5, 1979 [FI] Finland .................................. 790039

[51] Int. Cl.³ .............................................. B05B 7/30
[52] U.S. Cl. .................... 239/338; 128/200.21
[58] Field of Search ............... 239/337, 338, 370, 600; 128/200.14, 200.18, 200.21; 261/78 A, DIG. 65

[56] References Cited

U.S. PATENT DOCUMENTS

| | | | |
|---|---|---|---|
| 2,709,577 | 5/1955 | Pohndorf et al. | 239/338 X |
| 2,980,344 | 4/1961 | Marasco | 128/200.21 X |
| 3,591,090 | 7/1971 | Carden | 239/338 X |
| 3,744,722 | 7/1973 | Burns | 239/338 |
| 3,913,843 | 10/1975 | Cambio | 239/338 |
| 3,915,386 | 10/1975 | Vora | 239/338 |
| 4,061,698 | 12/1977 | Thornwald | 261/78 A |

*Primary Examiner*—Johnny D. Cherry
*Attorney, Agent, or Firm*—Steinberg & Raskin

[57] ABSTRACT

Apparatus for atomizing medicaments includes a hollow body member defining a pair of open ended connecting passages which branch therefrom, a container member coupled to the body member for containing the liquid medicament, a nozzle member connected to the body member adapted to be interconnected to an external source of pressure and having a suction tube attached thereto which extends into the container member and a fixing member for locating the nozzle member in its appropriate position. According to the invention, the nozzle and fixing members are provided as separate members, both of which are connected to the body member in a detachable manner so that the apparatus can be disassembled in order to clean the intervening space, i.e., the space in which the liquid medicament is admixed with a pressurized gas flow, defined within the nozzle member.

12 Claims, 5 Drawing Figures

APPARATUS FOR ATOMIZING MEDICAMENTS

BACKGROUND OF THE INVENTION

This invention relates to apparatus for atomizing liquid medicaments or drug atomizers and, more particularly, to apparatus of this type which include a body member provided with passages adapted to be connected to compressed gas and a mouthpiece or exhalation valve, a liquid medicament container and a nozzle assembly.

Conventional drug atomizers generally include a body member and a nozzle assembly which is either permanently fixed to or integral with the body member so that the nozzle assembly cannot be disassociated from the body member such, for example, as for cleaning purposes. Such nozzle assemblies generally include a nozzle portion and a fixing portion, the latter serving to locate the nozzle portion at its appropriate location. In fact, in conventional drug atomizers presently in use, the container in which the liquid medicament is located constitutes the only component which can be disassociated from the body member, the container generally being removably affixed thereto by means of screw threads or the like.

In view of the construction of conventional drug atomizers as described above, cleaning operations tend to be exceedingly awkward and difficult and, in fact, it is frequently impossible to clean such prior art apparatus in a satisfactory manner.

More particularly, drug atomizers presently in use include a so-called intervening space within the nozzle assembly into which the liquid medicament is drawn by suction and wherein the medicament is admixed with a pressurized gas flow. This intervening space communicates on one hand with an aperture formed in an inwardly extending connecting or juncture cone integral with the body portion of the atomizer and on the other hand with a slightly larger aperture provided in the nozzle assembly. During operation, bacteria and and various foreign matter tend to accumulate and due to the integral nature of the nozzle assembly with the body member, such accumulations cannot be easily removed if at all in a reliable manner. For example, where liquid cleaning agents are utilized, there is a possibility that toxic chemicals contained in such cleaning agents will be deposited and retained within the intervening space with the possibility that such chemicals will be entrained within the pressurized gas flow and introduced into the patient's lungs along with the inspired air or oxygen and atomized medicament when the atomizer is next used. Further, the bacteria which accumulates in the intervening space can also be carried along with the pressurized gas flow into the patient's lungs. Still further, if foreign matter is allowed to accumulate in the intervening space over a period of time, there is a possibility that the nozzle assembly will itself become completely occluded thereby preventing normal operation of the atomizer thereby resulting in a dangerous situation for the patient.

SUMMARY OF THE INVENTION

Accordingly, one object of the present invention is to provide a new and improved apparatus for atomizing liquid medicaments or drug atomizer.

Another object of the present invention is to provide a new and improved drug atomizer which can be thoroughly cleaned in a simple and reliable manner either in the hospital or elsewhere.

Briefly, in accordance with the present invention, these and other objects are attained by providing apparatus for atomizing liquid medicaments or a drug atomizer which includes a body member to which a container member is adapted to be coupled and to which a separate nozzle member and a separate nozzle fixing member are each detachably connected. In this manner, the nozzle assembly which comprises the separate nozzle and fixing member can be detached from the body member and themselves separated to provide access to the so-called intervening space as well as the nozzle member itself can be thoroughly cleaned in a simple and reliable manner.

In the illustrated preferred embodiment, the separate fixing member which serves to fix the nozzle member in the proper location is formed having a substantially cylindrical or sleeve-like configuration so as to have a skirt portion which surrounds the nozzle member so as to perform the additional function of a splash guard to prevent oversized liquid droplets from being carried into the outgoing connecting passage of the atomizer.

Further, the various components of the drug atomizer of the present invention are appropriately configured such that they can be easily disassembled and reassembled in a rapid manner. Each of the separate nozzle and fixing members as well as the body member to which they are detachably connected are relatively simple in design so that the drug atomizer of the present invention can be economically manufactured.

DESCRIPTION OF THE DRAWINGS

A more complete appreciation of the present invention and many of the attendant advantages thereof will be readily appreciated as the same becomes better understood by reference to the following detailed description when considered in connection with the accompanying drawings in which.

DESCRIPTION OF THE PREFERRED EMBODIMENT

Figure 1:
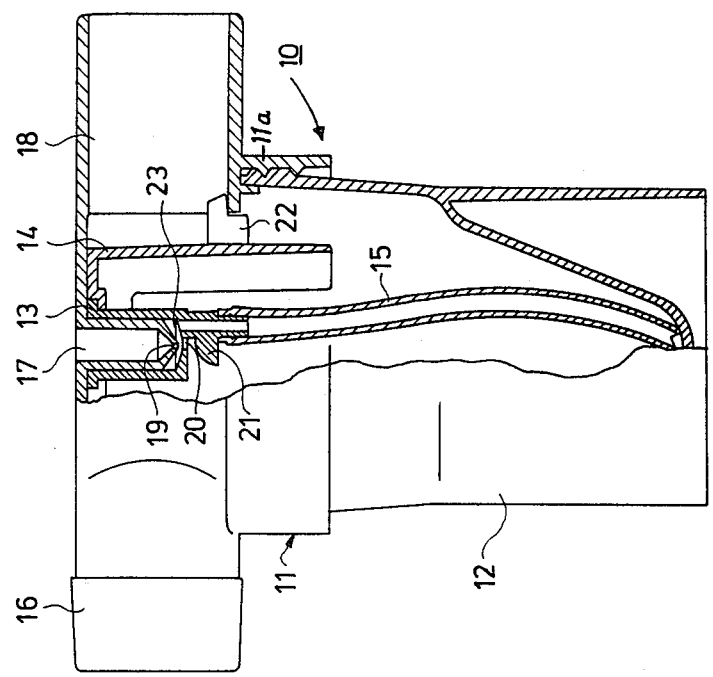
FIG. 1 is a front elevation view in partial section of the drug atomizer of the present invention.

Referring now to the drawings wherein like reference characters designate identical or corresponding parts throughout the several views, and more particularly to FIG. 1, apparatus for atomizing liquid medicaments or a drug atomizer according to the present invention is generally designated 10. The drug atomizer 10 generally includes a hollow cover or body member 11 having a downwardly extending internally threaded annular flange 11a to which a container member 12 is coupled by mating threads. The liquid medicament is carried within the container member 12 as is conventional. The body member 11 defines opposed connecting passages 16, 18, connecting passage 16 being adapted to be connected to a mouthpiece or exhalation valve while connecting passage 18 being adapted to be connected to a source of compressed air or oxygen.

An opening is formed at an upper central area in body member 11 from which a substantially cylindrical juncture cone 17 inwardly extends into the interior of the hollow body member 11. The inner end of juncture cone 17 tapers inwardly and an aperture 19 is provided at the apex thereof. The juncture cone 17 is adapted to receive a mating juncture cone of a pressure tube as in conventional.

According to the present invention, a separate nozzle member 13 is detachably connected to the body member 11 over the juncture cone 17 and is removably fixed in place by a separate nozzle fixing member 14 in a manner described in detail hereinbelow. A suction tube 15 has one end coupled to a connecting port 26 of nozzle member 13 and its other end extending into the container member 12 so as to be immersed in the liquid medicament contained therein.

Figure 4:
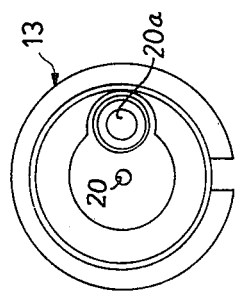
FIG. 4 is a plan view of a nozzle member for use in connection with the present invention.
Figure 5:
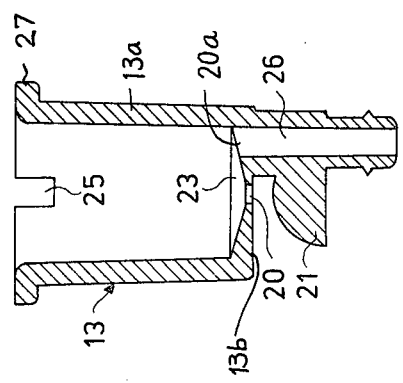
FIG. 5 is a elevation view in section of the nozzle member illustrated in FIG. 4.

Referring now to FIGS. 4 and 5 in conjunction with FIG. 1, the nozzle member 13 includes a generally cylindrical body portion 13a which tapers slightly inwardly as shown in FIG. 5 so as to snugly fit over the juncture cone 17 as seen in FIG. 1. A transversely extending bottom wall 13b has an inner surface which tapers inwardly and downwardly to an apex in which a nozzle aperture 20 is formed, nozzle aperture 20 being slightly larger in diameter than the aperture 19 formed in the juncture cone 17. A second aperture 20a is formed in bottom wall 13b adjacent to nozzle aperture 20 from which the connecting port 26 downwardly extends. A dispergator portion 21 is formed integrally with connecting port 26 and laterally extends beneath the nozzle aperture 20 for reasons which will be made clear hereinbelow in connection with the description of the operation of the drug atomizer. The upper end of nozzle member 13 has an outwardly directed annular shoulder 27 provided thereon and a slot 25 extends downwardly from the upper edge of nozzle member body portion 13a for a limited extent as illustrated in FIG. 5.

Figure 2:
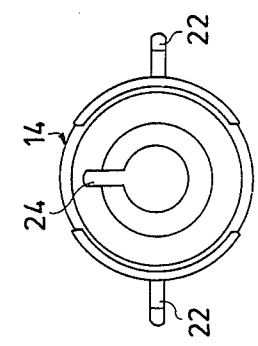
FIG. 2 is a plan view of the nozzle fixing member for use in the drug atomizer of the present invention.
Figure 3:
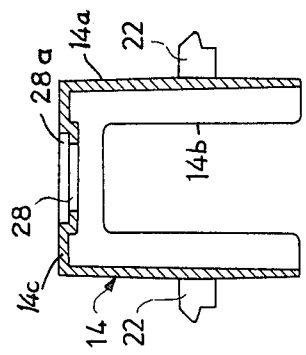
FIG. 3 is a elevation view in section of the nozzle fixing member illustrated in FIG. 2.

Referring to FIGS. 2 and 3 in conjunction with FIG. 1, the nozzle fixing member 14 is defined by a sleeve-like body portion 14a having a pair of opposed cutouts 14b formed therein. An upper transversely extending wall 14c closes the top end of fixing member 14. A shallow circular depression 28a is formed in the central area of the upper wall 14c of fixing member 14 in which a circular opening 28 is formed which is bounded on its perimeter by an annular recess formed by the depression 28a. A pair of bolt-like locking portions 22 are provided on diametrically opposed sides of the body portion 14a of fixing member 14. Finally, a guide portion 24 (FIG. 2) is formed at the upper end of fixing member 14.

In assembly, the nozzle member 13 is first inserted downwardly through the opening 28 into fixing member 14 until the annular shoulder 27 of the nozzle member is received within the annular recess formed by the depression 28a in the upper wall 14c as seen in FIG. 1. The slot 25 formed in nozzle member 13 receives the guide portion 24 formed on fixing member 14 to prevent the nozzle and fixing members from rotating with respect to each other, i.e., to rotatably fix one with respect to the other. The assembly thus formed is then inserted into the body member 11 (with the container member 12 disassociated therefrom). More particularly, the nozzle and fixing member assembly is located over the juncture cone 17, i.e., the juncture cone is received within the interior of the nozzle member 13 as seen in FIG. 1. The dimensions of the juncture cone 17 and nozzle member 13 are such that upon such positioning, the aperture 19 formed in juncture cone 17 and nozzle aperture 20 are vertically aligned and slightly spaced from each other, and further, an intervening space 23 is defined between the inner surface of the bottom wall 13b of nozzle member 13 and the downwardly tapering outer surface of juncture cone 17. Additionally, the bolt-like locking portions 22 formed on the nozzle fixing member 14 are affixed and secured to the walls defining the respective connecting passages 16, 18 on body member 11. The locking portions 22 thereby serve to fix the nozzle and fixing member assembly in the position illustrated in FIG. 1 i.e., located over the juncture cone 17. In positioning the locking portions 22 as described above, the nozzle and fixing member assembly is appropriately manipulated through the opening defined by the annular flange 11a formed on body member 11.

The mode of operation of the drug atomizer 10 of the present invention is the same as that of conventional drug atomizers currently in use. Thus, a source of pressure is connected with juncture cone 17 typically in the form of compressed air or oxygen whereupon the flow of the air or oxygen through the aperture 19 of the juncture cone 17 into the intervening space 23 produces a suction effect which draws the liquid medicament from the container member 12 through the suction tube 15, through the connecting port 26 and into the intervening space 23. The medicament is admixed with the pressurized flow of air or oxygen within the intervening space 23 and the liquid droplets so entrained by the pressure flow discharges from the intervening space 23 through the nozzle aperture 20 where they impinge on the dispergator portion 21 of the nozzle member 13. The surface of the dispergator portion 21 which faces the nozzle aperture 20 is preferably formed of a substantially spherical configuration so that when the liquid droplets impinge thereon, the same are dispersed into a fine liquid spray. The drug admixed as a spray with the air or oxygen flow then passes through the connecting branch 16 of the body member 11 into the mouthpiece as is conventional. The mouthpiece (not shown) may be preceded by a valve by which the counterpressure against exhalation can be adjusted in a continuous manner. The drug spray finally flows into the patient's lungs through the mouthpiece.

From the above, it is seen that the drug atomizer 10 of the present invention is such that the nozzle member 13 and the fixing member 14 can be removably attached to the body member 11. In this manner, it is possible to disassemble the atomizer 10 by removing the nozzle and fixing member assembly from the juncture cone 17 and then separating the nozzle member from the fixing member so that the surfaces defining the intervening space 23 can be reliably cleaned. Further, access to the apertures 19, 20 is provided in a manner not possible in conventional atomizers so that these may be cleaned or cleared of obstructions.

Further, by virtue of the particular structure of the fixing member described above, the body portion 14*a* thereof which as seen in FIG. 1 extends downwardly beyond the lower end of the nozzle member 13 and into the container member 12 can serve as a splash guard in order to prevent access of oversized liquid drops into the outgoing connecting branch 16.

Obviously, numerous modifications and variations of the present invention are possible in the light of the above teachings. Therefore, within the scope of the appended claims, it is understood that the invention may be practiced otherwise than is specifically disclosed herein.

What is claimed is:

1. Apparatus for atomizing liquid medicaments comprising:
   a hollow body member defining a pair of open ended connecting passages branching therefrom;
   a container member removably coupled to said body member for containing a liquid medicament;
   a separate nozzle member detachably connected directly to said body member defining an interior space therewithin and adapted to be interconnected to an external source of pressure, said nozzle member having a nozzle aperture and a connecting port, the latter being connectable to one end of a suction tube whose other end extends into said container member; and
   a separate fixing member detachably connected to said body member and separate nozzle member for detachably fixing the latter to said body member, said fixing member including a skirt portion which surrounds said nozzle member and functions as a splash guard for preventing access of oversized liquid drops into a connecting passage of the body member.

2. Apparatus as recited in claim 1 wherein said fixing member includes locking means for securing said fixing member to portions of said body member defining said connecting passages.

3. Apparatus as recited in claim 2 wherein said locking means comprise a pair of projecting bolt-like portions extending outwardly from said fixing member.

4. Apparatus as recited in claim 1 wherein said nozzle and fixing members include means for rotatably fixing one with respect to each other.

5. Apparatus as recited in claim 4 wherein said means for rotatably fixing said nozzle member with respect to said fixing member comprises a slot formed in said nozzle member and a guide portion formed on said fixing member, said slot adapted to receive said guide portion when said fixing member is detachably connected to said nozzle member.

6. Apparatus as recited in claim 1 wherein said fixing member has an opening formed therein having an annular recess surrounding the same, and wherein said nozzle member has an annular shoulder formed thereon, said nozzle member being received within said opening so that said shoulder is received in said recess.

7. Apparatus as recited in claim 1 wherein said body member includes an inwardly directed substantially cylindrical juncture cone defined therein having a juncture aperture formed therein and said nozzle member has a substantially cylindrical body portion adapted to fit over said juncture cone to define an intervening space therebetween and wherein said fixing member includes a locking portion adapted to be detachably secured to said body portion and a fixing portion adapted to hold said nozzle member in position.

8. Apparatus as recited in claim 1 wherein the nozzle aperture is formed in a lower end region of said nozzle member and said skirt portion extends downwardly beyond the lower end region of said nozzle member between the latter and the connecting passages of said body member.

9. Apparatus for atomizing liquid medicaments comprising:
   a hollow body member defining a pair of open ended connecting passages branching therefrom;
   a container member removably coupled to said body member for containing a liquid medicament;
   a separate nozzle member detachably connected to said body member defining an interior space therewithin and adapted to be interconnected to an external source of pressure, said nozzle member having a nozzle aperture and a connecting port, the latter being connectable to one end of a suction tube whose other end extends into said container member; and
   a separate fixing member detachably connected to said body member and separate nozzle member for detachably fixing the latter to said body member, said fixing member including locking means for securing said fixing member to portions of said body member defining said connecting passages, said locking means comprising a pair of projecting bolt-like portions extending outwardly from said fixing member.

10. Apparatus for atomizing liquid medicaments comprising:
    a hollow body member defining a pair of open ended connecting passages branching therefrom;
    a container member removably coupled to said body member for containing a liquid medicament;
    a separate nozzle member detachably connected to said body member defining an interior space therewithin and adapted to be interconnected to an external source of pressure, said nozzle member having a nozzle aperture and a connecting port, the latter being connectable to one end of a suction tube whose other end extends into said container member;
    a separate fixing member detachably connected to said body member and separate nozzle member for detachably fixing the latter to said body member; and
    said nozzle and fixing members including means for rotatably fixing one with respect to each other comprising a slot formed in said nozzle member and a guide portion formed on said fixing member, said slot adapted to receive said guide portion when said fixing member is detachably connected to said nozzle member.

11. Apparatus for atomizing liquid medicaments comprising:
    a hollow body member defining a pair of open ended connecting passages branching therefrom;
    a container member removably coupled to said body member for containing a liquid medicament;
    a separate nozzle member detachably connected to said body member defining an interior space therewithin and adapted to be interconnected to an external source of pressure, said nozzle member having a nozzle aperture and a connecting port, the latter being connectable to one end of a suction tube whose other end extends into said container member;
    a separate fixing member detachably connected to said body member and separate nozzle member for detachably fixing the latter to said body member; and
    wherein said fixing member has an opening formed therein having an annular recess surrounding the same, and wherein said nozzle member has an annular shoulder formed thereon, said nozzle member being received within said opening so that said shoulder is received in said recess.

12. Apparatus for atomizing liquid medicaments comprising:
 a hollow body member defining a pair of open ended connecting passages branching therefrom;
 a container member removably coupled to said body member for containing a liquid medicament;
 a separate nozzle member detachably connected to said body member defining an interior space therewithin and adapted to be interconnected to an external source of pressure, said nozzle member having a nozzle aperture and a connecting port, the latter being connectable to one end of a suction tube whose other end extends into said container member;
 a separate fixing member detachably connected to said body member and separate nozzle member for detachably fixing the latter to said body member; and
 wherein said body member includes an inwardly directed substantially cylindrical juncture cone defined therein having a juncture aperture formed therein and said nozzle member has a substantially cylindrical body portion adapted to fit over said juncture cone to define an intervening space therebetween and wherein said fixing member includes a locking portion adapted to be detachably secured to said body portion and a fixing portion adapted to hold said nozzle member in position.

* * * * *